United States Patent
Schmitt

(10) Patent No.: US 12,153,059 B2
(45) Date of Patent: Nov. 26, 2024

(54) PROCESS FOR PRODUCING A GASEOUS ACTIVE INGREDIENT OR A GASEOUS ACTIVE INGREDIENT MIXTURE, KIT FOR USE THEREIN AND GASEOUS COMPOSITION

(71) Applicant: Fritz Schmitt, Luxembourg (LU)

(72) Inventor: Fritz Schmitt, Luxembourg (LU)

(73) Assignee: Luxcan Innovation S.A., Luxembourg (LU)

( * ) Notice: Subject to any disclaimer, the term of this patent is extended or adjusted under 35 U.S.C. 154(b) by 688 days.

(21) Appl. No.: 17/421,058

(22) PCT Filed: Dec. 10, 2019

(86) PCT No.: PCT/DE2019/101065
§ 371 (c)(1),
(2) Date: Jul. 7, 2021

(87) PCT Pub. No.: WO2020/143863
PCT Pub. Date: Jul. 16, 2020

(65) Prior Publication Data
US 2022/0054769 A1  Feb. 24, 2022

(30) Foreign Application Priority Data

Jan. 7, 2019 (DE) .................... 10 2019 000 016.1
Jan. 7, 2019 (DE) .................... 10 2019 000 018.8
Jan. 15, 2019 (DE) .................... 10 2019 000 199.0

(51) Int. Cl.
*G01N 33/94* (2006.01)
*A24F 7/04* (2006.01)
(Continued)

(52) U.S. Cl.
CPC ............. *G01N 33/948* (2013.01); *A24F 7/04* (2013.01); *A24F 40/30* (2020.01); *A24F 40/42* (2020.01);
(Continued)

(58) Field of Classification Search
CPC ......... G01N 33/948; A24F 7/04; A24F 40/30; A24F 40/42; A24F 40/465; A24F 40/51;
(Continued)

(56) References Cited

U.S. PATENT DOCUMENTS

| 2,865,186 A | 12/1958 | Anderson et al. |
| 4,793,365 A | 12/1988 | Sensabaugh, Jr. et al. |

(Continued)

FOREIGN PATENT DOCUMENTS

| GB | 2561266 A | 10/2018 |
| JP | 2008104966 A | 5/2008 |

(Continued)

OTHER PUBLICATIONS

Mirko Heinemann. "Wirtschaftsfaktor Cannabis?—Legalisiemng konnte einen Wirtschaftsboom auslosen (Archiv)" Aug. 18, 2015 (Aug. 18, 2015), Retrieved from the Internet: https://www.deutschlandfunkkultur.de/wirtschaftsfaktor-cannabis-legalisierung-koennte-einen.976.de.html?dram:article_id=328530 [retrieved on Mar. 20, 2020] XP055678428, the whole document.

(Continued)

*Primary Examiner* — Alexander Gilman
(74) *Attorney, Agent, or Firm* — Harness, Dickey & Pierce, P.L.C.

(57) ABSTRACT

The present invention relates to a kit comprising: a) a bag having an outlet, the outlet being closable and openable; b) a solid and/or liquid active agent precursor; and c) means for releasing a gaseous active agent or a gaseous active agent mixture from the active agent precursor; a method for (Continued)

Figure 1:
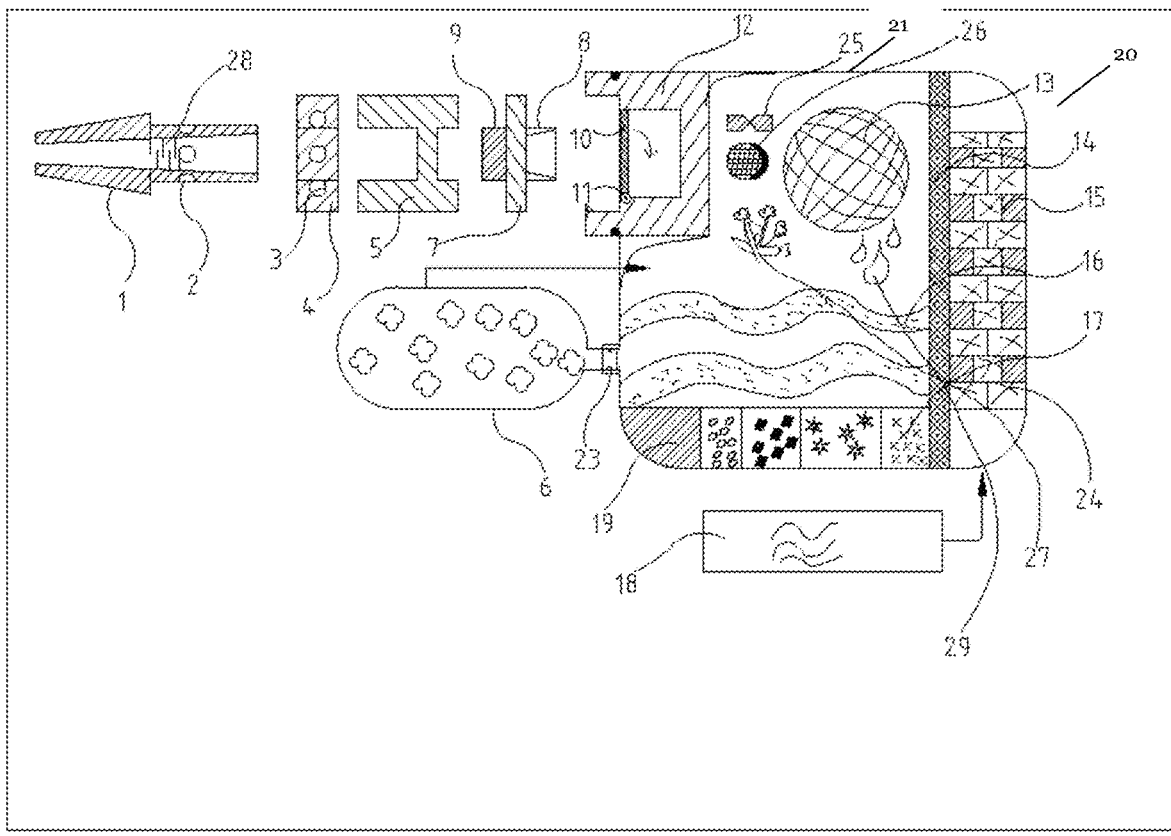

producing a gaseous active agent or a gaseous active agent mixture comprising the steps: a) providing the kit; b) providing the solid and/or liquid active ingredient precursor in the bag; and c) releasing the gaseous active ingredient or the gaseous active ingredient mixture from the solid and/or liquid active ingredient precursor with the aid of the means for releasing a gaseous active ingredient or a gaseous active ingredient mixture, and a gaseous composition obtainable by the process.

10 Claims, 1 Drawing Sheet

(51) Int. Cl.

| | |
|---|---|
| A24F 40/30 | (2020.01) |
| A24F 40/42 | (2020.01) |
| A24F 40/465 | (2020.01) |
| A24F 40/51 | (2020.01) |
| A24F 40/57 | (2020.01) |
| A24F 42/10 | (2020.01) |
| A24F 47/00 | (2020.01) |
| A61J 3/10 | (2006.01) |
| A61K 36/185 | (2006.01) |
| A61M 11/02 | (2006.01) |
| A61M 11/04 | (2006.01) |
| A61M 15/00 | (2006.01) |
| B01L 3/00 | (2006.01) |
| B30B 11/04 | (2006.01) |
| B30B 15/30 | (2006.01) |
| G01N 33/52 | (2006.01) |

(52) U.S. Cl.
CPC ........... *A24F 40/465* (2020.01); *A24F 40/51* (2020.01); *A24F 40/57* (2020.01); *A24F 42/10* (2020.01); *A24F 47/00* (2013.01); *A61J 3/10* (2013.01); *A61K 36/185* (2013.01); *A61M 11/02* (2013.01); *A61M 11/047* (2014.02); *A61M 15/0021* (2014.02); *A61M 15/0028* (2013.01); *B01L 3/502* (2013.01); *B01L 3/52* (2013.01); *B01L 3/523* (2013.01); *B30B 11/04* (2013.01); *B30B 15/302* (2013.01); *G01N 33/52* (2013.01); *A61M 11/041* (2013.01); *A61M 2205/3368* (2013.01); *A61M 2205/3686* (2013.01); *A61M 2205/6054* (2013.01); *A61M 2205/6072* (2013.01); *A61M 2205/609* (2013.01); *A61M 2205/75* (2013.01); *A61M 2206/20* (2013.01); *B01L 2300/069* (2013.01); *B01L 2300/0835* (2013.01); *B01L 2300/168* (2013.01); *B01L 2300/1816* (2013.01)

(58) Field of Classification Search
CPC .......... A24F 40/57; A24F 42/10; A24F 47/00; A61J 3/10; A61K 36/185; A61M 11/02; A61M 11/047; A61M 15/0021; A61M 15/0028
USPC ........................................................ 131/329
See application file for complete search history.

(56) References Cited

U.S. PATENT DOCUMENTS

| | | | |
|---|---|---|---|
| 5,101,839 A | 4/1992 | Jakob et al. | |
| 5,865,186 A * | 2/1999 | Volsey, II | A24F 42/10 131/194 |
| 10,300,228 B2 * | 5/2019 | Minskoff | A61M 15/0033 |
| 10,440,993 B2 * | 10/2019 | Minskoff | H05B 1/0244 |
| 10,994,085 B2 * | 5/2021 | Hogwood | A24F 40/42 |
| 2004/0118396 A1 * | 6/2004 | Hughes | A61M 15/009 128/200.14 |
| 2008/0241255 A1 * | 10/2008 | Rose | A24F 42/20 514/343 |
| 2012/0006342 A1 * | 1/2012 | Rose | A24F 42/60 131/273 |
| 2012/0103326 A1 * | 5/2012 | Karle | A61D 7/04 128/200.21 |
| 2013/0239964 A1 * | 9/2013 | Young | A61M 15/0003 128/203.12 |
| 2014/0144429 A1 * | 5/2014 | Wensley | A61M 15/06 128/200.14 |
| 2014/0182587 A1 * | 7/2014 | Dunne | B65D 47/283 128/203.15 |
| 2014/0261486 A1 * | 9/2014 | Potter | A24F 40/30 131/328 |
| 2015/0114409 A1 * | 4/2015 | Brammer | A61M 15/025 |
| 2015/0136131 A1 | 5/2015 | Holakovsky et al. | |
| 2016/0228658 A1 * | 8/2016 | Minskoff | A61M 15/0033 |
| 2017/0196262 A1 * | 7/2017 | Brereton | A24F 42/60 |
| 2017/0368273 A1 * | 12/2017 | Rubin | A61M 16/0093 |
| 2018/0160732 A1 * | 6/2018 | Bless | A24F 40/42 |
| 2018/0220708 A1 * | 8/2018 | Scott | A24F 40/46 |
| 2018/0271150 A1 | 9/2018 | Sparklin et al. | |
| 2020/0261653 A1 * | 8/2020 | Schmitt | A61M 5/31583 |
| 2020/0353171 A1 | 11/2020 | Schmitt | |
| 2020/0360611 A1 | 11/2020 | Schmitt | |

FOREIGN PATENT DOCUMENTS

| | | |
|---|---|---|
| WO | 98/57556 A1 | 12/1998 |
| WO | WO-2016033242 A1 | 3/2016 |
| WO | WO-2018216019 A1 | 11/2018 |
| WO | WO-2019003118 A1 | 1/2019 |

OTHER PUBLICATIONS

Grotenhermen, F and Müller-Vahl, K: The Therapeutic Potential of Cannabis and Cannabinoids, Dtsch Arztebl Int 2021; 109(29-30); 495-501, DOI: 10.3238/arztebl.2012.0495.
International Search Report (English and German) and Written Opinion (German) of the International Searching Authority issued in PCT/DE2019/101065, mailed Apr. 1, 2020; ISA/EP.

* cited by examiner

PROCESS FOR PRODUCING A GASEOUS ACTIVE INGREDIENT OR A GASEOUS ACTIVE INGREDIENT MIXTURE, KIT FOR USE THEREIN AND GASEOUS COMPOSITION

CROSS-REFERENCE TO RELATED APPLICATIONS

This application is a U.S. National Phase Application under 35 U.S.C. 371 of International Application No. PCT/DE2019/101065, filed on Dec. 10, 2019, which claims the benefit of German Application No. 10 2019 000 0199.0, filed on Jan. 15, 2019, and German Application No. 10 2019 000 016.1, filed on Jan. 7, 2019, and German Application No. 10 2019 000 018.8, filed on Jan. 7, 2019. The entire disclosures of the above applications are incorporated herein by reference.

BACKGROUND

This section provides background information related to the present disclosure which is not necessarily prior art.

TECHNICAL FIELD

The present invention relates to a process for producing a gaseous active agent or a gaseous mixture of active agents, a kit for use in said process, and a gaseous composition obtainable by said process.

DISCUSSION

The legalization of *Cannabis* and its use as a medicine raise many questions about safe and easy administration and the provision of appropriate forms of administration by pharmacists and physicians.

A large number of different devices are known from the prior art which attempt to heat substances, herbs or liquids at a specific temperature using hot air, hot plates or glow wires in such a way that the desired active ingredient is available for inhalation. Most known devices operate on the "hot plate principle." That is, plant parts containing an active ingredient are spread over a heated surface in the hope that vaporization of the ingredients will occur in the process. This method works poorly because the substances in direct contact with the heated surface are heated much more than the substances in the layers above it, which means that uniform evaporation of the ingredients is not possible.

In another functional principle, plant parts are flown through with air heated to a certain temperature range. The plant parts then steam out their ingredients—assuming the necessary minimum temperature—which can then be inhaled after cooling. Especially when used in the medical field, these devices cannot guarantee device safety. All requirements for a medical device are missing, since the device cannot be sterilized. However, this is urgently necessary considering the combustion residues to be expected on the heating plates ("grill grates").

SUMMARY

This section provides a general summary of the disclosure, and is not a comprehensive disclosure of its full scope or all of its features.

It is therefore one aspect of the present invention to provide a method for releasing active substances from corresponding precursor mixtures which overcomes disadvantages of the prior art, in particular is suitable for releasing active substances from corresponding precursor mixtures in a gentle manner, by means which satisfy medical standards.

This aspect is first solved by a kit comprising: a) a bag having an outlet, said outlet being closable and openable; b) a solid and/or liquid active agent precursor; and c) means for releasing a gaseous active agent or a gaseous active agent mixture from said active agent precursor.

The kit according to the invention makes it possible in a simple and gentle manner to release a gaseous active ingredient from a solid and/or liquid active ingredient precursor. Here, it may be provided that the active ingredient is a pharmacologically active ingredient. After release, the gaseous active ingredient, or the gaseous active ingredient mixture, can be aspirated or inhaled for medical purposes. It is known that inhalation of an active ingredient is particularly efficient, as this saves the route through the stomach (in the case of oral administration) or the portal vein circulation (in the case of injection). In addition, active ingredient absorption is supported by absorption via the oral mucosa. The kit according to the invention and the method according to the invention (as described further below) enable the patient to take up a pharmacologically active agent in the lungs, where it acts locally or rapidly enters the bloodstream via the alveoli and acts systematically there. With local therapy, side effects in the rest of the organism can be reduced and a lower dose is required, since a larger proportion of the dose reaches the site of action than with peroral administration. However, even if the drug is to enter the bloodstream for systemic action, a lower dose is usually required because the first-pass effect in the liver is bypassed. Due to the large absorption area of the lungs (approx. 70-100 square meters) and the thin epithelial layer, active substances reach the body more quickly and can take effect earlier than with peroral administration.

Another advantage of the kit according to the invention is its flexibility. Depending on the patient and his needs, the active substance precursor can be prepared individually and tailored to the patient by the pharmacist and then made available in the kit for application.

In one embodiment, it may be provided that the active ingredient precursor is arranged in the bag. The amount of active ingredient precursor can be adjusted depending on the patient in such a way that the amount of gaseous active ingredient released from the active ingredient precursor corresponds approximately to the lung volume of the patient (for example, lung volume +/−10% vol.). In this context, it may be envisaged that the amount of gaseous active ingredient released is 10 times, preferably 20 times, particularly preferably 30 times the total volume of the bag. In this way, a particularly effective application of the gaseous active substance tailored to the patient can be achieved.

In one embodiment, it may be provided that the active ingredient precursor comprises a *Cannabis* flower, marijuana, hashish, hashish oil, at least one cannabinoid, or a mixture thereof.

*Cannabis* (hemp), together with the genus *Humulus* (hops), belongs to the family Cannabisaceae, although *Humulus* does not contain cannabinoids. Within the genus *Cannabis*, a botanical and chemotaxonomic differentiation is made into the species *Cannabis sativa* Linnaeus, *Cannabis* indica LAM and *Cannabis ruderalis* or into the "collective species" *Cannabis sativa* L., consisting of the subspecies *Cannabis sativa* ssp. *sativa* and ssp. indica. In addition, *Cannabis* is divided into a drug and fiber hemp, with the distinction based on the quantitative ratio of the main cannabinoids cannabidiol (CBD) and Δ9-tetrahydrocannabinol (Δ9-THC) (INN: dronabinol). Fiber hemp (also: commercial hemp, industrial hemp) is mainly used for industrial fiber production and may have a maximum Δ9-THC content of 0.2% (e.g. Germany et al.), while the drug type may have a Δ9-THC content of about 5-15% (marijuana, hashish). *Cannabis sativa* L. contains over 400 different constituents, of which more than 60 compounds belong to the class of cannabinoids. The most important cannabinoids are shown below:

Cannabigerol-like (CBG): Cannabigerol ((E)-CBG-C5), Cannabigerol monomethyl ether ((E)-CBGM-C5 A), Cannabinerolic acid A ((Z)-CBGA-C5 A), Cannabigerovarin ((E)-CBGV-C3), Cannabigerolic acid A ((E)-CBGA-C5 A), Cannabigerolic acid A monomethyl ether ((E)-CBGAM-C5 A), Cannabigerovaric acid A ((E)-CBGVA-C3 A);

Cannabichromene-like (CBC): cannabichromene (CBC-C5), cannabichromic acid A (CBCA-C5 A), cannabichromevarin (CBCV-C3), cannabichromevarinic acid A (CBCVA-C3 A);

Cannabidiol-like (CBD): cannabidiol (CBD-C5), cannabidiol monomethyl ether (CBDM-C5), cannabidiol-C4 (CBD-C4), cannabidivarin (CBDV-C3), cannabidiorcol (CBD-C1), cannabidiolic acid (CBDA-C5), cannabidivaric acid (CBDVA-C3);

Cannabinodiol-like (CBND): Cannabinodiol (CBND-C5), Cannabinodivarin (CBND-C3);

Tetrahydrocannabinol-like (THC): Δ9-tetrahydrocannabinol (Δ9-THC-C5), Δ9-tetrahydrocannabinol-C4 (Δ9-THC-C4), Δ9-tetrahydrocannabivarin (Δ9-THCV-C3), Δ9-tetrahydrocannabiorcol (Δ9-THCO-C1), Δ9-tetrahydrocannabinolic acid (Δ9-THCA-C5 A), Δ9-tetrahydrocannabinolic acid B (Δ9-THCA-C5 B), Δ9-tetrahydrocannabinolic acid-C4 (Δ9-THCA-C4 A and/or B), Δ9-tetrahydrocannabivaric acid A (Δ9-THCVA-C3 A), Δ9-tetrahydrocannabiorcolic acid (Δ9-THCOA-C1 A and/or B), (−)-Δ8-trans-(6aR,10aR)-Δ8-tetrahydrocannabinol (Δ8-THC-C5), (−)-Δ8-trans-(6aR,10aR)-tetrahydrocannabinolic acid A (Δ8-THCA-C5 A); (−)-(6aS,10aR)-Δ9-tetrahydrocannabinol ((−)-cis-Δ9-THC-C5);

Cannabinol-like (CBN): cannabinol CBN-C5, cannabinol-C4 (CBN-C4), cannabivarin (CBN-C3), cannabinol-C2 (CBN-C2), cannabiorcol (CBN-C1), cannabinolic acid A (CBNA-C5 A), cannabinol methyl ether (CBNM-C5).

Cannabitriol-like (CBT): (−)-(9R,10R)-trans-cannabitriol ((−)-trans-CBT-C5), (+)-(9S,10S)-cannabitriol ((+)-trans-CBT-C5), (±)-(9R,10S/9S,10R)-cannabitriol ((±)-cis-CBT-C5), (−)-(9R,10R)-trans[10-0-Ethyl-cannabitriol] ((−)-*trans-CBT-OEt-C5*), (±)-(9R,10R/9S,10S)-Cannabitriol-C3 ((±)-*trans-CBT-C3*),8,9-dihydroxy-Δ6a(10a) tetrahydrocannabinol (8,9-di-OH-CBT-C5), cannabidiolic acid A (CBDA-C5 9-OH-CBT-C5 ester), (−)-(6aR,9S,10S,10aR)-9,10-dihydroxy-hexahydrocannabinol, Cannabiripsol Cannabiripsol-C5, (−)-6a,7,10a-trihydroxy-Δ9-tetrahydrocannabinol ((−)-cannabitetrol), 10-Oxo-Δ6a(10a) tetrahydrocannabinol (OTHC);

Cannabielsoin-like (CBE): (5aS,6S,9R,9aR)-C5-cannabielsoine (CBE-C5), (5aS,6S,9R,9aR)-C3-cannabielsoine (CBE-C3), (5aS,6S,9R,9aR)-cannabielsoic acid A (CBEA-C5 A), (5aS,6S,9R,9aR)-cannabielsoic acid B (CBEA-C5 B), (5aS,6S,9R,9aR)-C3-cannabielsoic acid B (CBEA-C3 B), cannabiglendol-C3 (OH-iso-HHCV-C3), dehydrocannabifuran (DCBF-C5), cannabifuran (CBF-C5);

Isocannabinoids: (−)-Δ7-trans-(1R,3R,6R)-isotetrahydrocannabinol, (±)-Δ7-1,2-cis-(1R,3R,6S/1S,3S,6R)-isotetrahydrocannabivarin, (−)-Δ7-trans-(1R,3R,6R)-isotetrahydrocannabivarin;

Cannabicyclol-like (CBL): (±)-(1aS,3aR,8bR,8cR-cannabicyclol (CBL-C5), (±)-(1aS,3aR,8bR,8cR-cannabicyclic acid A (CBLA-C5 A), (±)-(1aS,3aR,8bR,8cR-cannabicyclovarin (CBLV-C3);

Cannabicitran-like (CBT): Cannabicitran (CBT-C5);

Cannabichromanone-like (CBCN): cannabichromanone (CBCN-C5), cannabichromanone-C3 (CBCN-C3), cannabicoumaronone (CBCON-C5).

In addition to the cannabinoids mentioned above, their associated carboxylic acids are found in the crude drug. These carboxylic acids are biosynthetic precursors.

*Cannabis* preparations exert a variety of therapeutic effects, including antispasmodic, analgesic, antiemetic, neuroprotective, anti-inflammatory, and effects in psychiatric disorders (Grotenhermen F, Müller-Vahl K: The therapeutic potential of *Cannabis* and cannabinoids.

In Germany, a *Cannabis* extract containing THC (dronabinol) and CBD in a 1:1 ratio (Nabiximols) has been approved for the treatment of moderate to severe therapy-resistant spasticity in multiple sclerosis (MS) as a sublingual spray (Sativex) since 2011.

Cannabidiol (CBD, CBD-C5) is the major non-psychotropic cannabinoid of the genus *Cannabis* and CBD is not a cannabinoid receptor agonist.

FIG. 1: CBD (structural formula)

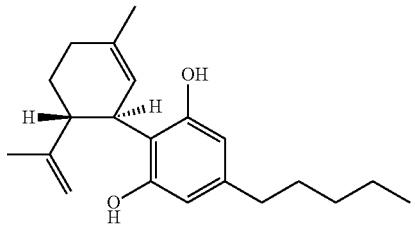 [SMILES: C=C(C)[C@@H]1CCC(C)=C[C@H]1c1c(O)cc(CCCCC)cc1O]

CBD can be produced synthetically (Michoulam R, Shvo Y., Hashish. I. The structure of cannabidiol, Tetrahedron. 1963, 19(12), 2073).

The outlet can be closed and opened. This means that the outlet can be opened, for example by applying a vacuum (suction) or by a mechanical mechanism, to allow the gaseous active ingredient or the gaseous active ingredient mixture to escape from the bag for application, and then closed again to store the remaining gaseous active ingredient, or the remaining gaseous active ingredient mixture, in the bag.

In one embodiment, it may be provided that the outlet comprises a mouthpiece. Alternatively, it may be provided that the outlet comprises means for connecting the outlet to a mouthpiece. A mouthpiece in this case is a tube-like component through which a gas can be transported, for example by negative pressure (suction). In this way, the application of the released gaseous active substance is facilitated.

In this context, it can be provided that the mouthpiece is a part of the outlet, i.e. the outlet together with the mouthpiece is a monolithic component that is connected to the bag. Likewise, it may be provided that the outlet and the mouthpiece are two different parts that can be connected to each other, for example by screwing, clicking, etc. of the mouthpiece to the outlet. Furthermore, it may be provided that the combination of the outlet and the mouthpiece comprises further components, such as rotatable sleeves, plug-in connections, hinges and further components that serve to connect them. In particular, it may be provided that the outlet, if it does not monolithically comprise the mouthpiece, further comprises a mouthpiece holder. It may be provided that the mouthpiece and/or the outlet are multi-part, wherein the individual parts forming the mouthpiece and/or the outlet are connectable to each other.

In a further embodiment, it may be provided that the mouthpiece comprises an air inlet. It may further be provided that the mouthpiece additionally comprises an air inlet regulation. In this way, the concentration of the amount of ambient air and gaseous active ingredient from the bag can be regulated in a simple manner.

In one embodiment, it may be provided that the outlet comprises a piercing cannula and/or a piercing membrane. This can be particularly effective in ensuring that no active ingredient (prior to application of the gaseous active ingredient or the gaseous active ingredient mixture) escapes unintentionally.

The means for releasing a gaseous active ingredient or a gaseous active ingredient mixture from the active ingredient precursor can be arranged outside the bag or inside the bag. Likewise, it may be provided that the means for releasing a gaseous active ingredient or a gaseous active ingredient mixture from the active ingredient precursor are connected to the bag, or constitute a part of the bag. In one embodiment, it may be provided that the means for releasing a gaseous active ingredient or a gaseous active ingredient mixture are arranged in the bag and/or are connected to the bag.

In principle, the means for releasing a gaseous active ingredient or a gaseous active ingredient mixture from the active ingredient precursor are not limited as long as they allow a relevant pharmacologically active ingredient to be released from the solid and/or liquid active ingredient precursor. Suitable are the following means, or means that allow one or more of the following process steps to be carried out:
 Extraction
 Distillation
 Pressing
 Fractionation
 Cleaning
 Enrichment
 Fermentation
 Temperature
 Ultrasound
 Electromagnetic waves
 Bacteria
 Mushrooms In one embodiment, it may be provided that the means for releasing a gaseous active agent or a gaseous mixture of active agents comprises a heating element, preferably a chemical heating element.

The heating element may comprise, for example, a heating coil, preferably made of platinum or gold foil. The metal foil has a similar function to a heating wire in a light bulb, but cannot burn out. A heating coil placed in the bag can be powered by a rechargeable battery, usually with a lithium-ion cell.

A chemical heater is a heater in which heat is generated by an exothermic reaction of one or more compounds (heat-generating composition; heat-generating reactant) contained in the heater. For example, it may be provided that an acid anhydride or an acid salt and a basic anhydride or a basic salt are used as the reaction agent, wherein the basic salt may be selected from the group consisting of sodium acetate, sodium benzoate, and potassium ascorbate. Further, may comprise an inert material selected from the group consisting of an oil, a wax, a surfactant.

In the case where the chemical heating element contains two different compounds that react with each other in an exothermic reaction, it may be provided that, prior to activation, these compounds are present in different reservoirs that prevent the compounds from inadvertently mixing and reacting. Actuation of an opening element opens the reservoirs so that the two reactants come into contact and react, releasing heat. Contact between the two materials results in an exothermic chemical reaction. Alternatively, a first reservoir may contain a fuel, such as alcohol, and the second reservoir may contain an oxidizing agent, such as permanganate compounds, so that a heat-generating chemical reaction also occurs when the two materials are in contact. The use of a chemical heating element allows the kit of the invention to be used independently of a power supply.

In one embodiment, it may be provided that the bag comprises a film, preferably made of one or more plastics, preferably selected from the group consisting of polyethylene terephthalate, polyethylene terephthalate copolyester with isophthalic acid and diethylene glycol, polyethylene naphthalate, polyethylene furanoate, polylactide and mixtures thereof. Hereby, safe and easy bag fabrication can be achieved.

In a further embodiment, it may be provided that the bag comprises a first chamber and a second chamber, the first chamber containing the solid and/or liquid drug precursor and being connected to the second chamber; and the outlet is arranged at the second chamber. This can prevent solid and/or liquid portions of the active ingredient precursor from reaching the outlet in an undesirable manner.

The first chamber can be made of a thermoplastic film, in particular PET, PET copolyester with isophthalic acid and diethylene glycol, PET, PEN, PEF, PLA. The second chamber can be made of a film or aluminum foil with one, two or more layers, an aluminum foil, optionally coated on one or two sides with a film, or the like.

In a further embodiment, it may be provided that the bag further comprises a connector suitable for connecting an auxiliary tank to the bag. The additional tank may store, for example, oxygen or other gaseous substances. The connector enables these additional substances to be introduced into the bag in a simple manner.

In a further embodiment, it may be provided that the bag has a permeability to carbon dioxide of more than $1.0*10-2$ ml/(cm2*atm*day) and preferably more than $2.0*10-2$ m)/(cm2*atm*day). Likewise, it may be provided that the bag has a gas permeability for the gaseous active agent, or gaseous mixture of active agents, of less than $10*10-2$ ml/(cm2*atm*day).

In addition, a variety of other embodiments may contribute to the advantageous design of the invention.

It may be provided that the bag, in particular the outlet thereof, includes a child safety device.

It may be provided that the bag is made of a fabric, in particular using carbon fibers.

It may be provided that the bag is made of a film.

It may be provided that the bag is made of a material that reacts with a color change to a change in temperature.

It may be provided that the kit further comprises a thermometer that indicates the temperature within the bag.

It may be provided that the heating element is made by mercury vapor.

It may be envisaged that heat is generated in the heating element, in particular in the chemical heating element, by a catalyst effect.

It may be provided that the solid active ingredient precursor comprises ground *Cannabis* flowers, preferably in a flour-like embodiment. It may be provided that the solid and/or liquid active ingredient precursor is at least partially arranged in the form of a coating on the inner side of the pouch. In particular, it may be provided that the inner side of the pouch is coated with ground *Cannabis* flowers, in particular in a flour-like embodiment. This achieves a particularly high specific surface area of the active ingredient precursor and thus facilitates gas release.

It may be provided that the gaseous active ingredient, or the gaseous active ingredient mixture, is a drug and/or vaccine. In this way, for example, a natural process can be achieved.

It may be provided that the kit comprises a propellant composition in the form of a heating unit, nutrient solution and microorganisms, or herbs & flowers.

In a further embodiment, it may be provided that the first chamber is made of a barrier-free thermoplastic film, and herbs, flowers and plant constituents or nutrient solution and microorganisms are accommodated therein, the microorganisms being capable of releasing active ingredients by fermentation, and the second container is arranged at the outlet and serves to accommodate and mix the composition to be dispensed and/or a plurality of second containers are provided one inside the other, which may, for example, have the shape of spheres.

It may be provided that the bag is gas-tight.

It may be provided that the solid and/or liquid active ingredient precursor is placed in the bag together with functional elements (wherein the functional elements may comprise, but are not necessarily limited to, means for releasing a gaseous active ingredient or a gaseous active ingredient mixture) and the functional elements may be externally controlled to serve a release of the gaseous active ingredient or the release of the gaseous active ingredient mixture, respectively.

It may be provided that the inside of the bag is provided with a coating suitable for binding gaseous substances that are not the gaseous active ingredient or are not contained in the gaseous active ingredient mixture.

The aspect is further solved by a method for producing a gaseous active ingredient or a gaseous active ingredient mixture, comprising the steps of: a) providing a kit according to one of the preceding claims; b) providing the solid and/or liquid active ingredient precursor in the bag; and c) releasing the gaseous active ingredient or the gaseous active ingredient mixture from the solid and/or liquid active ingredient precursor with the aid of the means for releasing a gaseous active ingredient or a gaseous active ingredient mixture.

In this regard, it may be provided that the releasing comprises heating the solid and/or liquid drug precursor.

In this context, it may be provided that the solid and/or liquid active ingredient precursor is heated during the heating process to a temperature in a range from 170 to 220° C., preferably 180° C. to 210° C., particularly preferably 185 to 210° C.

Those who ingest *Cannabis* for medicinal purposes want to release as many cannabinoids (especially THC and CBD) from the hemp plant as possible. However, these cannabinoids are not present in the hemp plant in their effective pure form, but as so-called carboxylic acids (THCA and CBDA). These carboxylic acids must be converted to THC and CBD. This is achieved by means of so-called decarboxylation. In this process, one molecule of carbon dioxide is split off from each of the carboxylic acids THCA and CBDA. What remains are the desired compounds THC and CBD.

Decarboxylation can be initiated with heat. Therefore, when vaporizing *Cannabis* using the present invention, setting the proper vaporization temperature is ensured by electronic adjustment. This should be between preferably between 180 and 210 degrees Celsius.

The following process steps can be applied: *Cannabis* is first heated to exactly 180° C. with electromagnetic waves, sensors control the temperature to within 1°. The temperature can be increased to 210° C. to dissolve as many cannabinoids as possible. Of course, the use of *Cannabis* oil or extracts is also possible.

Another advantage of the process according to the invention is that the apartment remains odor-free. Anyone who smokes *Cannabis* in their home must expect the smell of the smoke to be perceptible for days to come. This risk does not exist with vaporization.

Burning of the flowers can be prevented by ensuring that the heating process takes place in the absence of oxygen.

*Cannabis* flowers can be crushed before use. Grinding balls that can be moved with the help of magnets are suitable for this purpose. An increase in the effect is achieved by heating the metal balls inductively.

According to the invention, *Cannabis* can be combined with other medicinal plants depending on the therapy. This is easy to realize with the present method, because the bag can be combined several times with different chambers. Due to the entourage effect, the effect of *Cannabis* can be supported in this case.

It may be envisaged that the kit comprises further functional elements. The following functional elements may be mentioned by way of example.

Material for binding liquid
Filter materials
Heating elements
Mechanical grinders
all materials that exert a chemical or mechanical reaction
Elements that are statically charged
Centrifuge
Catalyst
UV filter Finally, the aspect is solved by a gaseous composition obtainable by the process according to the invention, wherein the active ingredient precursor comprises a *Cannabis* flower, marijuana, hashish, hashish oil, at least one cannabinoid or a mixture thereof; and the solid and/or liquid active ingredient precursor is heated during heating to a temperature in a range of 170 to 220° C., preferably 180° C. to 210° C., particularly preferably 185 to 210° C.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

In the following, the invention will be described with reference to the drawings by means of specific embodiments. It is to be understood here that the reference to the specific embodiments serves merely to illustrate the invention. The features of the specific embodiments are not necessarily limiting for the invention, but may, in particular in combination with the embodiments mentioned in the foregoing, contribute to the advantageous realization of the invention.

FIG. 1: is a schematic representation of a kit according to one embodiment of the invention.

DETAILED DESCRIPTION

Example embodiments will now be described more fully with reference to the accompanying drawings.

In FIG. 1, the reference signs have the following meaning:
1 Mouthpiece
2 Air inlet
3 Air inlet regulation
4 Cuff, rotatable
5 Mouthpiece holder
6 Auxiliary tank
7 Plug connection
8 Piercing cannula
9 Connecting element
10 Piercing membrane
11 Hinge
12 Outlet
13 fine mesh basket for flowers or other bio material
14 Chemical heating element
15 Heating elements
16 Liquid active ingredients
17 active ingredients incorporated into the bag
18 External power generator
19 Buckling element, triggers chemical reaction
20 Kit
21 Bag sleeve
23 Connection for external filling
24 Heating element
25 metal leaf to bend, triggers chemical reaction
26 Pollutant vacuum cleaner with activated carbon filter
27 Biomaterial, such as *Cannabis* flower
28 Filters
29 Liquid active ingredients In the embodiment shown in FIG. 1, a large number of features and elements which can contribute to the advantageous realization of the invention are shown simultaneously. It will be understood by those skilled in the art that not all of the features (components, etc.) shown in FIG. 1 need necessarily be present simultaneously to realize a device according to the invention.

FIG. 1 shows a kit 20 according to the invention. This comprises a bag 21 with an outlet 12 and various means 14, 15, 18, 19, 24, 25 for releasing a gaseous active ingredient or a gaseous active ingredient mixture from the active ingredient precursor. Solid active agent precursor 27 and liquid active agent precursor 16, 29 are contained in the bag 21. If the solid active ingredient precursor 27 is a material that is finely divided, such as a powdered material, it may be present in a fine mesh basket 13. Further solid active ingredient precursor is incorporated into a portion of the bag 17. Mechanical action on the portion of the bag 17 may release the active ingredient precursor contained therein.

The outlet 12 shown in FIG. 1 comprises a piercing membrane 10 and a hinge 11 that connects the piercing membrane 10 to the outlet 12 in a manner that the latter is movably arranged. The outlet 12 is configured to be connected to a mouthpiece 1 and other parts, namely a cuff 4, a mouthpiece holder 5 and a connector 7. The mouthpiece 1 comprises an air inlet 2 as well as a filter 28. With the cuff 4, an air inlet regulation 3 is arranged between the mouthpiece 1 and the outlet 12. Together with the plug-in connection 7, a connecting element 9 and a piercing cannula 8 are arranged between the outlet 12 and the mouthpiece holder 5.

In FIG. 1, various means for releasing a gaseous active agent or a gaseous mixture of active agents from the active agent precursor are shown. For example, an external energy generator 18 is shown, which may be a heater arranged outside the bag. Also shown are chemical heating elements 14, further heating elements 15, a buckling element 19 that can initiate an exothermic chemical reaction, a further heating element 24, and a metal plate 25 that can be buckled to initiate an exothermic chemical reaction.

In addition, the bag 21 includes a pollutant aspirator 26 provided with an activated carbon filter. Finally, the bag has a connection 23 that allows the bag 21 to be filled with material from an auxiliary tank 6.

The features disclosed in the foregoing description and the appended claims may, separately or in combination, be subject matter for realizing aspects of the disclosure made in the independent claims in various forms thereof.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A kit, comprising:
  a. a bag having an outlet, the outlet being closable and openable;
  b. a solid and/or liquid active ingredient precursor; and
  c. Means for releasing a gaseous active ingredient or a gaseous mixture of active ingredients from the active ingredient precursor,
  wherein:
  d. the solid and/or liquid active ingredient precursor is at least partially arranged in the form of a coating on the inner side of the bag.

2. The kit of claim 1, wherein the active ingredient precursor comprises a *Cannabis* flower, marijuana, hashish, hashish oil, at least one cannabinoid, or a mixture thereof.

3. The kit according to claim 1, wherein the outlet comprises a mouthpiece.

4. The kit of claim 1, wherein the outlet comprises means for connecting the outlet to a mouthpiece.

5. The kit according to claim 1, wherein the means for releasing a gaseous active ingredient or a gaseous mixture of active ingredients comprises a heating element.

6. The kit according to claim 1, wherein the bag comprises a first chamber and a second chamber, wherein
  the first chamber contains the solid and/or liquid active ingredient precursor and is connected to the second chamber; and
  the outlet is arranged at the second chamber.

7. A method for producing a gaseous active ingredient or a gaseous mixture of active ingredients, comprising:
  a. Providing a kit according to claim 1;
  b. Providing the solid and/or liquid active ingredient precursor in the bag; and
  c. Releasing the gaseous active ingredient or the gaseous mixture of active ingredients from the solid and/or liquid active ingredient precursor with the aid of the means for releasing a gaseous active ingredient or a gaseous mixture of active ingredients.

8. The method of claim 7, wherein the releasing comprises heating the solid and/or liquid active ingredient precursor.

9. The process according to claim 8, wherein the solid and/or liquid active ingredient precursor is heated to a temperature in a range of 170 to 220° C., preferably 185 to 210° C., during heating.

10. A gaseous composition obtainable by a process according to claim 7, wherein
- the active ingredient precursor comprises a *Cannabis* flower, marijuana, hashish, hashish oil, at least one cannabinoid, or a mixture thereof; and
- the solid and/or liquid active ingredient precursor is heated to a temperature in a range from 170 to 220° C., preferably 185 to 210° C., during the heating process.

\* \* \* \* \*